United States Patent
Shelton

(10) Patent No.: US 12,286,451 B2
(45) Date of Patent: Apr. 29, 2025

(54) BORATE ESTER COMPLEXES OF α-HYDROXY CARBOXYLIC ACIDS AND THEIR CONJUGATE BASE BUFFERS

(71) Applicant: Medtech Products Inc., Irvington, NY (US)

(72) Inventor: Mackenzie Shelton, Gretna, VA (US)

(73) Assignee: MEDTECH PRODUCTS INC., Tarrytown, NY (US)

(*) Notice: Subject to any disclaimer, the term of this patent is extended or adjusted under 35 U.S.C. 154(b) by 66 days.

(21) Appl. No.: 17/532,712

(22) Filed: Nov. 22, 2021

(65) Prior Publication Data

US 2022/0162234 A1    May 26, 2022

Related U.S. Application Data

(60) Provisional application No. 63/139,136, filed on Jan. 19, 2021, provisional application No. 63/117,166, filed on Nov. 23, 2020.

(51) Int. Cl.
*C07F 5/04* (2006.01)
*A61K 9/00* (2006.01)

(52) U.S. Cl.
CPC ............ *C07F 5/04* (2013.01); *A61K 9/0014* (2013.01)

(58) Field of Classification Search
CPC ...................................................... C07F 5/04
See application file for complete search history.

(56) References Cited

U.S. PATENT DOCUMENTS

| | | | |
|---|---|---|---|
| 5,468,414 A | 11/1995 | Panandiker et al. |
| 8,920,786 B2 | 12/2014 | Hloucha et al. |
| 9,018,150 B1 | 4/2015 | Rizk |
| 10,722,440 B2 | 7/2020 | Schroeder et al. |
| 2011/0166057 A1 | 7/2011 | Lenoir |
| 2015/0265528 A1 | 9/2015 | Shapiro et al. |
| 2016/0120803 A1 | 5/2016 | Mathur et al. |
| 2019/0314258 A1 | 10/2019 | Laurent et al. |
| 2019/0365623 A1 | 12/2019 | Botto |

FOREIGN PATENT DOCUMENTS

| | | |
|---|---|---|
| CA | 2137268 | 12/1993 |
| CA | 2128581 | 2/1995 |
| CA | 2208500 | 6/1996 |
| CA | 2543370 | 5/2004 |
| CA | 2583874 | 4/2006 |
| CA | 2709208 | 6/2009 |
| CA | 2208246 | 11/2009 |
| CA | 2414941 | 12/2010 |
| CA | 2398224 | 5/2011 |
| CA | 2793876 | 9/2011 |
| CA | 2494427 | 1/2013 |
| CA | 2633489 | 9/2013 |
| CA | 2730309 | 3/2014 |
| CA | 2883403 | 3/2014 |
| CA | 3000088 | 4/2017 |
| CA | 3026904 | 12/2017 |
| CA | 3047186 | 6/2018 |
| CA | 3057569 | 10/2018 |
| CA | 3060378 | 11/2018 |
| CA | 2916897 | 4/2019 |
| CA | 3086082 | 6/2019 |
| CA | 3096374 | 10/2019 |
| CA | 3017661 | 3/2020 |
| CN | 102993433 | 5/2015 |
| EP | 0742220 | 6/1999 |
| EP | 1372383 | 7/2008 |
| WO | 2004105710 | 12/2004 |
| WO | 2012044416 | 4/2012 |
| WO | 2018191221 A1 | 10/2018 |
| WO | 2019030458 | 2/2019 |

OTHER PUBLICATIONS

Larsson, R. and Nunziata, G. "An Infrared Spectroscopic Investigation on the Complexes formed between Boric Acid and Lactic Acid in Aqueous Solution." Acta Chemica Scandinavica. (1970), vol. 24, pp. 2156-2168. (Year: 1970).*
Pizer, Richard, et al. "The Boric Acid/Lactic Acid System. Equilibria and Reaction Mechanism." Inorganic Chemistry. (1984), vol. 23, No. 19, pp. 3023-3026. (Year: 1984).*
Houston, et al., "Tapping Into Boron/ a-Hydroxycarboxylic Acid Interactions in Sensing and Catalysis", Aust. J. Chem., 2007, 60, 811-815.
Houston, et al., "Boric Acid-Catalyzed, Chemoselective Esterification of a-Hydroxycarboxylic Acids", Organic Letters, Apr. 2004, 5 pages.

* cited by examiner

*Primary Examiner* — John S Kenyon
(74) *Attorney, Agent, or Firm* — Taylor English Duma LLP

(57) ABSTRACT

A composition is provided for use as a buffer in personal care and pharmaceutical formulations. The composition comprises complex esters of boric acid and simple α-hydroxy carboxylic acids, and the corresponding basic conjugate salts of complex esters of boric acid and simple α-hydroxy carboxylic acids. The weight of boric acid and α-hydroxy acid is up to about 1.0% by weight (w/w %) of the composition. The molar ratio of boric acid to α-hydroxy acid is between about 1:1 and about 1:2. The composition may be formulated for topical application. Formulations comprising the composition include a personal lubricant, wound cream, feminine cleansing douche, moisturizing lotion, a wipe, and a cleansing wash. A method of treating the skin is also provided, the method comprising the step of topically applying onto the skin an effective amount of the composition.

21 Claims, 6 Drawing Sheets

BORATE ESTER COMPLEXES OF α-HYDROXY CARBOXYLIC ACIDS AND THEIR CONJUGATE BASE BUFFERS

CROSS-REFERENCES TO RELATED APPLICATIONS

This application is related to U.S. provisional application No. 63/117,166, filed Nov. 23, 2020, and U.S. provisional application No. 63/139,136, filed Jan. 19, 2021, both entitled "Borate Ester Complexes of α-Hydroxy Carboxylic Acids and their Conjugate Base Buffers", and both naming Mackenzie Shelton as the inventor. The contents of the two provisional applications are incorporated herein by reference in their entirety, and the benefit of the filing dates of the provisional applications is hereby claimed for all purposes that are legally served by such claims for the benefit of the filing dates.

BACKGROUND

Ligand exchange reaction products of boric acid and simple α-hydroxy carboxylic acids and their conjugate base buffers are described and, more particularly, their use as buffers for topical personal care and pharmaceutical formulations.

The use of α-hydroxy acids in topical formulations is ubiquitous because the buffering ranges are appropriate for skin. However, there is always a risk of excess skin cell proliferation due to absorption α-hydroxy acids. The formation of boric acid ester complexes and their conjugate bases can increase buffering capacity as compared to the parent α-hydroxy acid. The exception can be found in the more complex case of citric acid. Although there is evidence of the borate ester complexes forming due to the reduction in pKa when compared to the parent α-hydroxy acid, there is no increase in the buffering capacity observed due to the greater complexity associated with polyprotic α-hydroxy acids.

Boric acid complex esters have been reported by Larsson and Nunziata, *An Infrared Spectroscopic Investigation on the Complexes formed between Boric Acid and Lactic Acid in Aqueous Solution*, Acta Chemica Scandinavica 24 (1970). Pfizer and Seizer reported the reaction between boric acid and α-hydroxy carboxylic acids yields two different recognized complexes, the 1:1 molar and the 1:2 molar equivalents; Boric Acid/Lactic Acid System. Equilibria and Reaction Mechanism, Inorganic Chemistry 23 (1984). The formation of the 1:1 ester is the product of an addition and substitution reaction. The 1:2 ester involves a substitution reaction of a borate anion. The reaction mechanism is therefore pH driven and the 1:1 ester is strongly favored at high pH, whereas the 1:2 ester is favored at low pH. This pH dependence of ester formation allows for the stabilization of pH balanced formulations based on the buffering capacity derived from the boric acid in conjunction with an α-hydroxy carboxylic acid. Not to be bound by a specific theory, the equilibria gives preference to ester formation in aqueous media, enough to favorably reduce the volatility of the α-hydroxy carboxylic acid. The borate ester complexes, be they monoester, 1:1, diester, 1:2 or sesquiester, 1:1.5, all provide equivalent pH buffering performance for simple α-hydroxy acids.

For the foregoing reasons, there is a need for borate ester complexes of α-hydroxy carboxylic acids and their conjugate base buffers for use in topical and pharmaceutical formulations. Ideally, the new borate ester complexes and their conjugate base buffers will enable fragrance-free formulations without the sour note associated with carboxylic acids.

SUMMARY

A composition for use as a buffer in personal care and pharmaceutical formulations is provided. The composition comprises complex esters of boric acid and simple α-hydroxy carboxylic acids, and corresponding basic conjugate salts of complex esters of boric acid and simple α-hydroxy carboxylic acids. In one embodiment, the complex esters are selected from mono complex esters, di complex esters, or a mixture of mono complex esters and di complex esters.

In certain aspects, the weight of boric acid and α-hydroxy acid is up to about 1.0% by weight (w/w %) of the composition, the weight of boric acid and α-hydroxy acid is up to about 0.5% by weight (w/w %) of the composition, or the weight of boric acid and α-hydroxy acid is up to about 0.4% by weight (w/w %) of the composition.

In certain aspects, the molar ratio of boric acid to α-hydroxy acid is between about 1:1 and about 1:2, the molar ratio of boric acid to α-hydroxy acid is between about 1:1.2 and about 1.8, or the molar ratio of boric acid to α-hydroxy acid is between about 1:1.4 and about 1:1.6

The composition may be formulated for topical application. Accordingly, a method is provided for treating the skin comprising the step of topically applying onto the skin an effective amount of the composition.

A formulation is provided for use as a personal lubricant, the formulation comprising the composition up to about 1% by weight of the formulation, and further comprising sodium benzoate up to about 0.50% by weight of the formulation, xanthan gum up to about 1.0% by weight of the formulation, hyaluronic acid up to about 0.5% by weight of the formulation, and aloe vera gel up to about 0.5% by weight of the formulation. The composition for the personal lubricant formulation may comprise a lactic acid ester complex.

A formulation is provided for use as a wound cream, the formulation comprising the composition up to about 1% by weight of the formulation, and further comprising glycerin up to about 5% by weight of the formulation, dipalmitoylethyl hydroxyethylmonium methosulfate up to about 3% by weight of the formulation, emulsifying wax up to about 3.5% by weight of the formulation, isopropyl myristate up to about 3% by weight of the formulation, dimethicone up to about 1.25% by weight of the formulation, cetyl alcohol up to about 2% by weight of the formulation, and lanolin up to about 2% by weight of the formulation, and potassium chloride up to about 0.35% by weight of the formulation. The composition for the wound cream formulation may comprise a lactic acid ester complex.

A formulation is provided for use as a feminine cleansing douche, the formulation comprising the composition up to about 5% by weight of the formulation, and further comprising sodium benzoate up to about 1% by weight of the formulation, edetate disodium up to about 0.5% by weight of the formulation and vinegar up to about 0.5% by weight of the formulation. The composition for the cleansing douche formulation may comprise a lactic acid ester complex.

A formulation is provided for use as a moisturizing lotion, the formulation comprising the composition up to about 4% by weight of the formulation, and further comprising acrylates/C10-C30 alkyl acrylate crosspolymer up to about 0.55% by weight of the formulation, sunflower seed oil up to about 1% by weight of the formulation, PEG 40 HCO up to about 0.5% by weight of the formulation, aminomethyl propanol 2000 up to about 0.9% by weight of the formulation, sorbitol monolaurate up to about 1% by weight of the formulation, hemisqualane up to about 2.5% by weight of the formulation, and phenoxyethanol up to about 0.75% by weight of the formulation. The composition for the moisturizing formulation may comprise a lactic acid ester complex.

A formulation is provided for use as a wipe, the formulation comprising the composition up to about 1.13% by weight of the formulation, and further comprising decyl glucoside up to about 1% by weight of the formulation, sodium benzoate up to about 0.5% by weight of the formulation, and edetate disodium up to about 0.5% by weight of the formulation. The composition for the wipe formulation may comprise a lactic acid ester complex.

A formulation is provided for use as a cleansing wash, the formulation comprising the composition up to about 10% by weight of the formulation, and further comprising sodium c14-c16 olefin sulfonate up to about 20% by weight of the formulation, cocamidopropyl hydroxysultaine up to about 15% by weight of the formulation, sodium methyl cocoyl taurate up to about 5% by weight of the formulation, guar hydroxypropyltrimonium chloride up to about 0.05% by weight of the formulation, sodium benzoate up to about 1% by weight of the formulation, and sodium chloride up to about 1% by weight of the formulation. The cleansing wash formulation may comprise a lactic acid ester complex.

In another embodiment, a composition for use as buffers in personal care and pharmaceutical formulations comprises mono complex esters of boric acid and simple α-hydroxycarboxylic acids, di complex esters of boric acid and simple α-hydroxycarboxylic acids, sesquihydroxycarboxylic acids of boric acid, α-hydroxycarboxylic acids, and their corresponding basic conjugate salts. In aspect, the composition may further comprise mono complex esters of lactic acid, di complex esters of lactic acid, sesquihydroxycarboxylic acids of lactic acid, and their corresponding basic conjugate salts. The composition may be in the acidic range of about 3.8-5.8 and the corresponding salts are in the basic range of about 8.2-10.2, or the acidic range of about 4.0-5.5 and the corresponding salts are in the basic range of about 8.4-9.9.

DESCRIPTION

Figure 1:
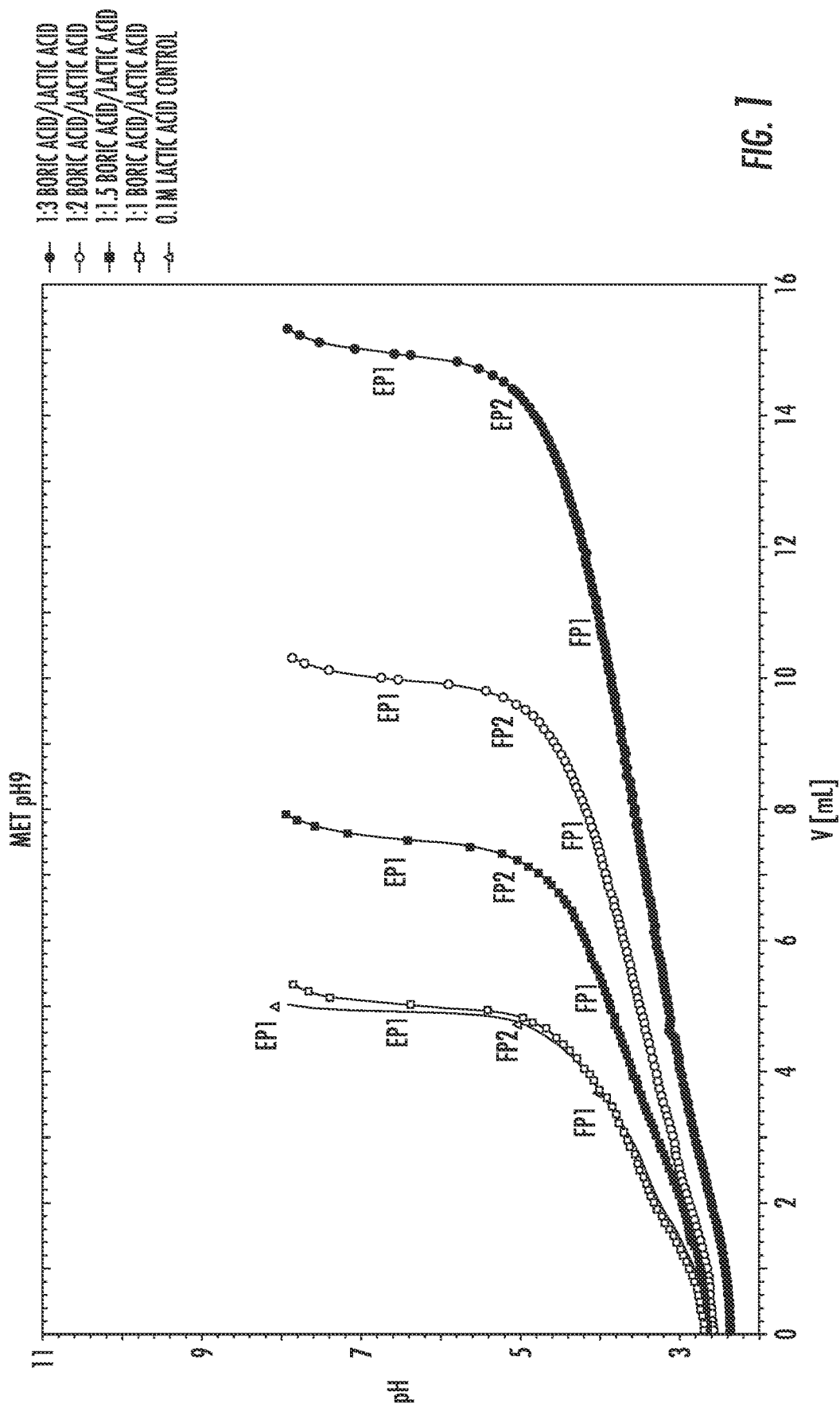
FIG. 1 is a graph showing boric acid/lactic acid molar titrations of reaction products of boric acid and α-hydroxy carboxylic acids.
Figure 2:
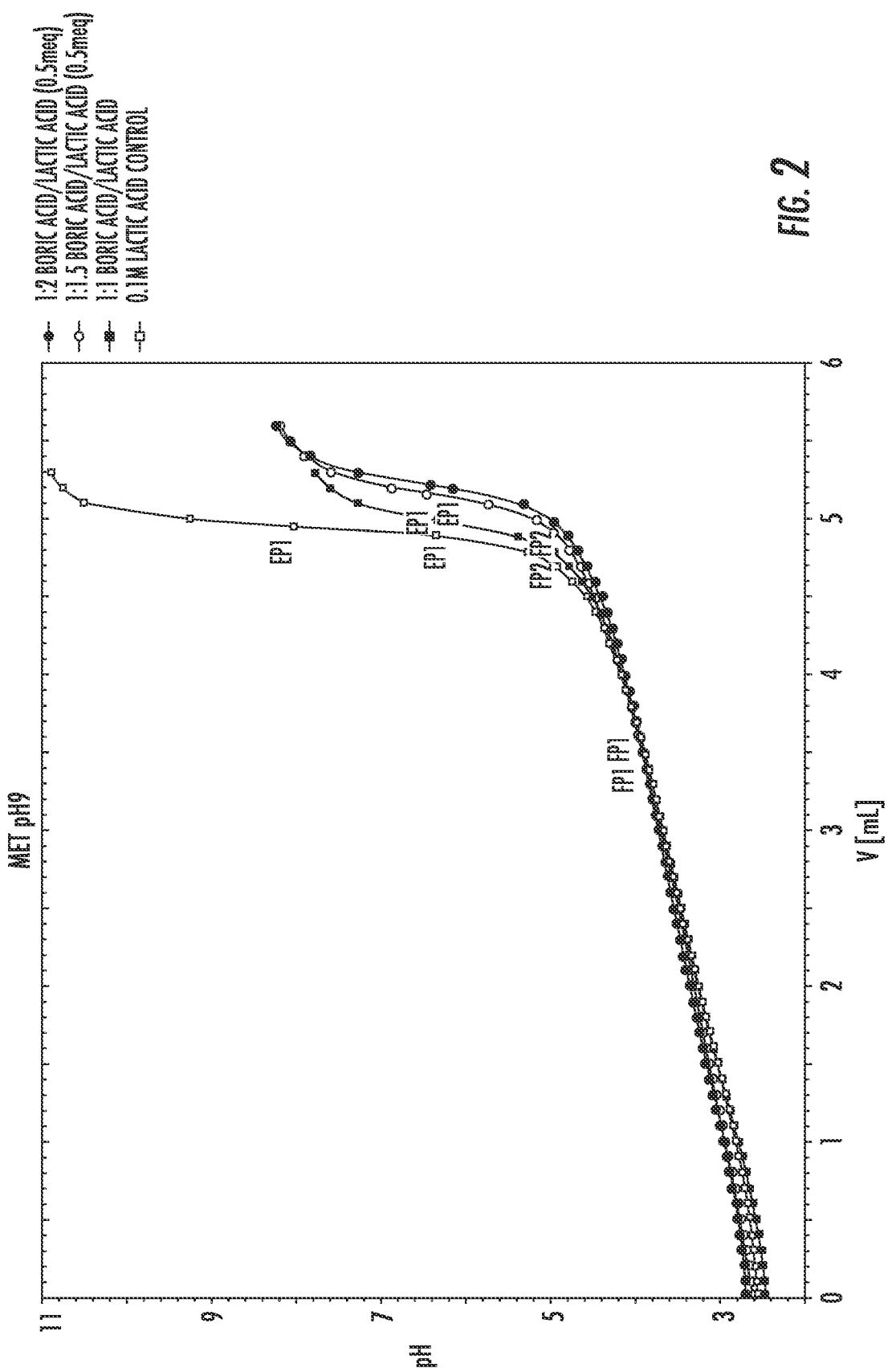
FIG. 2 is a graph showing boric acid/lactic acid equivalent titrations of reaction products of boric acid and α-hydroxy carboxylic acids.
Figure 3:
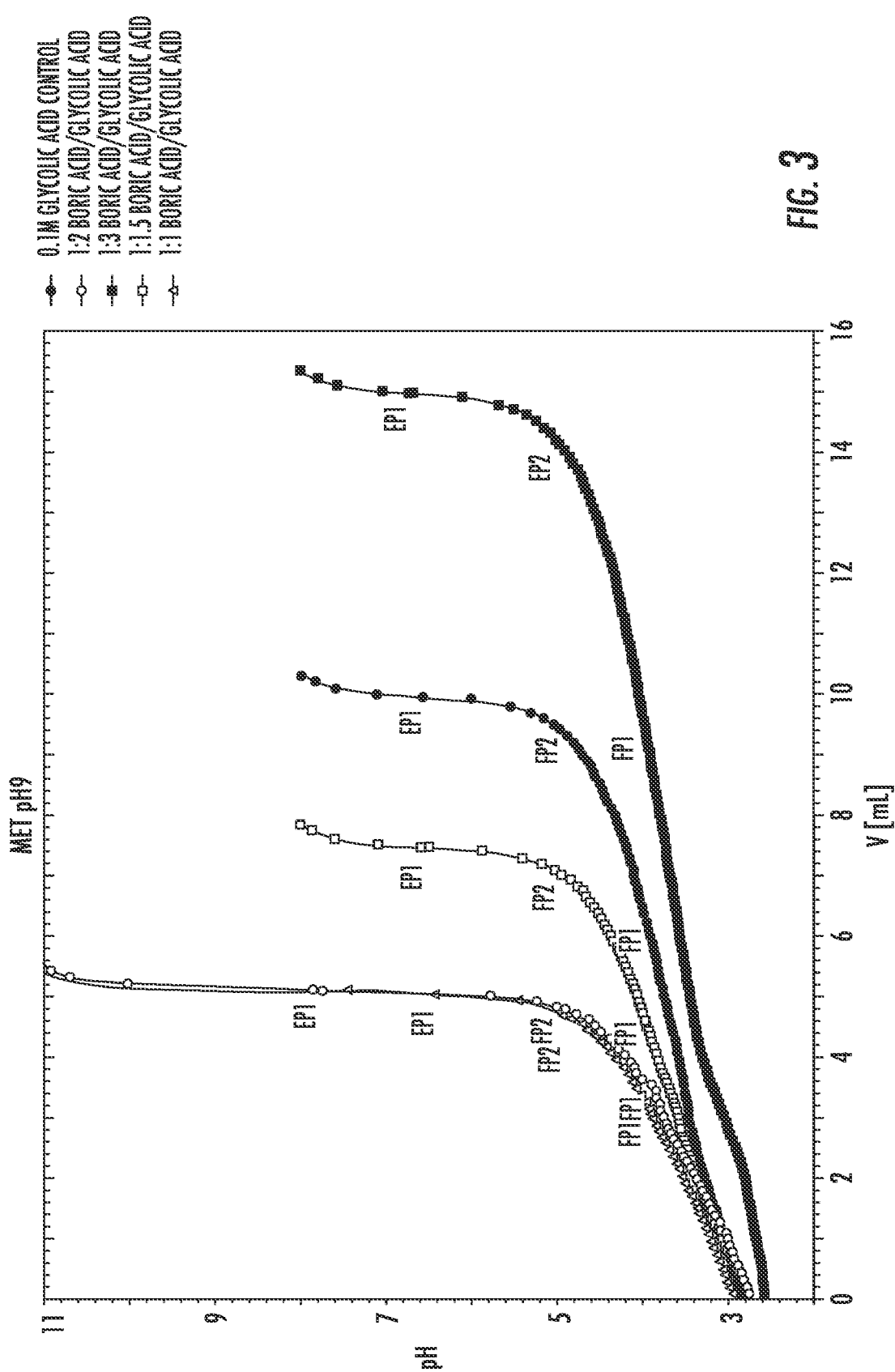
FIG. 3 is a graph showing boric acid/glycolic acid molar titrations of reaction products of boric acid and α-hydroxy carboxylic acids.
Figure 4:
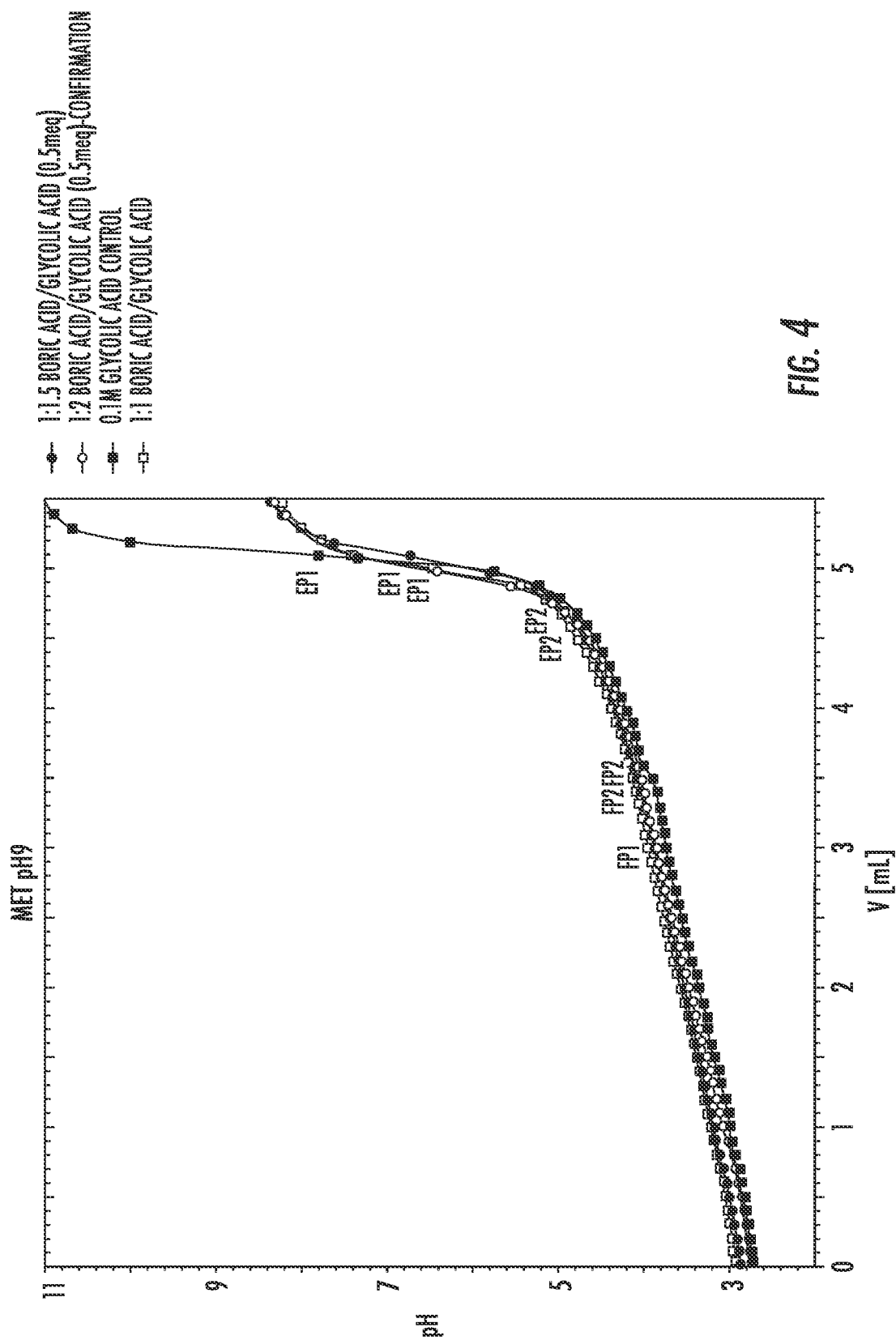
FIG. 4 is a graph showing boric acid/glycolic acid equivalent titrations of reaction products of boric acid and α-hydroxy carboxylic acids.
Figure 5:
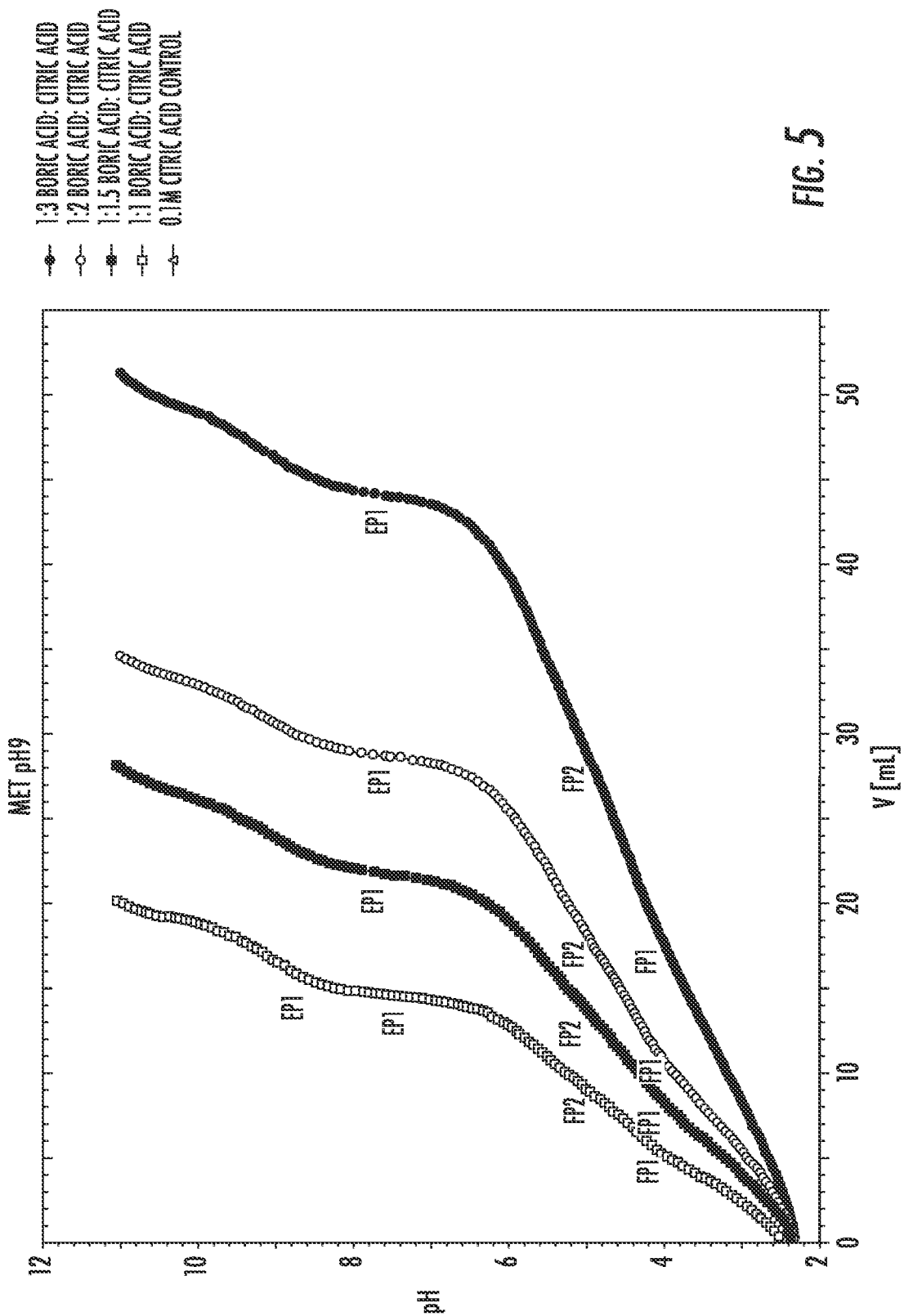
FIG. 5 is a graph showing citric acid molar titrations of reaction products of boric acid and α-hydroxy carboxylic acids.
Figure 6:
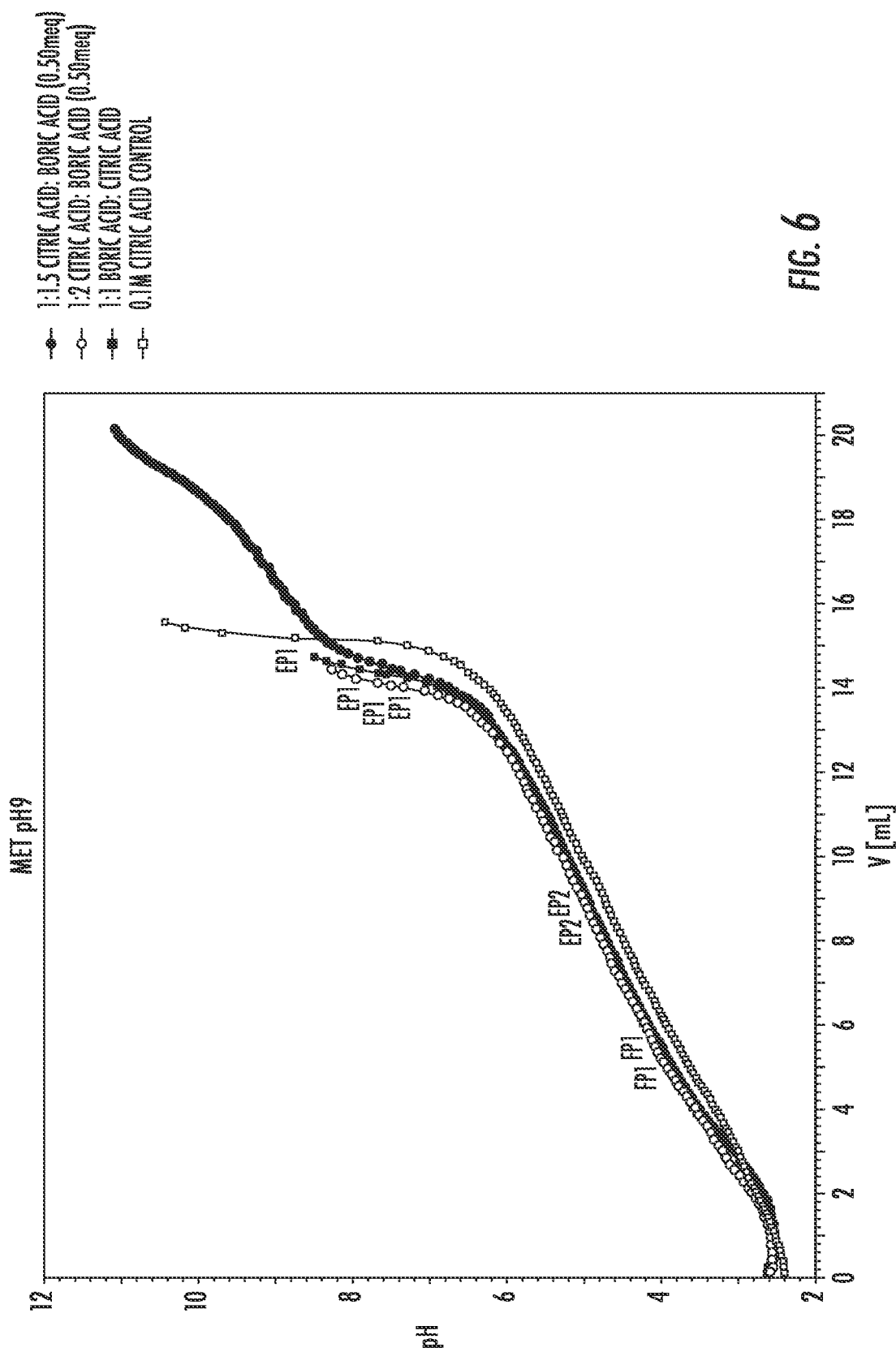
FIG. 6 is a graph showing citric acid equivalent titrations of reaction products of boric acid and α-hydroxy carboxylic acids.

Ligand exchange reaction products of boric acid and simple α-hydroxy carboxylic acids are described. In one embodiment, the borate ester complexes of α-hydroxy carboxylic acids and their conjugate base buffers are useful as buffers for topical personal care and in pharmaceutical formulations.

The boric acid ester complexes and their conjugate bases provide excellent buffering within desirable ranges for topical formulations. The borate ester complexes increase buffer capacity without significant change to the buffering range. Not to be bound by a specific theory, the formation of the borate ester complexes allows for a unique buffering effect beneficial in low pH topical cosmetic and pharmaceutical formulations. The complexes have lower pKa values and greater buffer capacity than the parent α-hydroxy carboxylic acid. In the present application, the formulator is able to achieve equivalent pH stability using less α-hydroxy acid content, lowering the risk of skin cell turnover. Surprisingly, the borate ester complexes are odorless, eliminating the sour note the acids impart to the unfragranced base. Stability samples of a fragrance-free personal wash held at 40 centigrade for three months remained odor free with no noticeable change and no apparent buildup of volatile lactic or glycolic acid in the sample headspace.

Reaction products of boric acid and α-hydroxy carboxylic acids were prepared by diluting pre-made stock solution of 0.4M boric acid and 0.4M, 0.6M, and 0.8M α-hydroxy carboxylic acid.

TABLE 1

Dilution Table (100 ml reaction product)

| Test Ratio | Boric Acid | α-hydroxy acid | Water |
|---|---|---|---|
| Control | 0 ml | 25 ml, 0.4M | 75 ml |
| 1:1 | 25 ml | 25 ml, 0.4M | 50 ml |
| 1:1.5 | 25 ml | 25 ml, 0.6M | 50 ml |
| 1:2 | 25 ml | 25 ml, 0.8M | 50 ml |
| 1:3 | 25 ml | 50 ml, 0.6M | 25 ml |

Each reaction mixture was allowed to mix for a minimum of two hours before subsequent titration with 0.1N certified sodium hydroxide solution. Two sets of titrations were performed. The first set of titrations, molar titration, 5.0 ml of each solution is titrated to accurately determine end point and the pKa and pH at half of the end point. The second set of titrations, equivalence titration, solution volumes were adjusted to 0.5 milliequivalent and the buffer capacity determined. For simplicity, buffer capacity is reported as the milliequivalents of titrant required to raise the pH one unit from the pKa value. An exception was made for the 1:3 test ratio in which free α-hydroxy acid and the boric acid ester complex could not be distinguished between.

In the control titration, α-hydroxy acid pKa values were reasonably close to literature reported values. The values for the complex borate esters are surprisingly all equivalent and significantly different from the parent α-hydroxy acid, with the exception of buffer capacity examples with citric acid. Surprisingly, borate ester samples did not exhibit a sour odor usually associated with the simpler α-hydroxy acids.

TABLE 2

Lactic Acid Molar Titrations

| Test Ratio | 0 | 1:1 | 1:1.5 | 1:2 | 1:3 |
|---|---|---|---|---|---|
| pKa | 4.0 | 3.2 | 3.2 | 3.2 | N/A |
| Capacity | 11 | 23 | 23 | 24 | N/A |
| Odor | slight odor | very slight odor | odorless | very slight odor | slight odor |

TABLE 3

Lactic Acid Equivalent Titrations

| Test Ratio | 0 | 1:1 | 1:1.5 | 1:2 | 1:3 |
|---|---|---|---|---|---|
| pKa | 4.0 | 3.2 | 3.2 | 3.2 | N/A |
| Capacity | 11 | 23 | 26 | 27 | N/A |
| Odor | slight odor | very slight odor | odorless | very slight odor | slight odor |

TABLE 4

Glycolic Acid Molar Titrations

| Test Ratio | 0 | 1:1 | 1:1.5 | 1:2 | 1:3 |
|---|---|---|---|---|---|
| pKa | 3.9 | 3.2 | 3.3 | 3.3 | N/A |
| Capacity | 13 | 29 | 29 | 29 | N/A |
| Odor | slight odor | very slight odor | odorless | very slight odor | slight odor |

TABLE 5

Glycolic Acid Equivalent Titrations

| Test Ratio | 0 | 1:1 | 1:1.5 | 1:2 | 1:3 |
|---|---|---|---|---|---|
| pKa | 3.9 | 3.2 | 3.2 | 3.3 | N/A |
| Capacity | 13 | 29 | 27 | 28 | N/A |
| Odor | slight odor | very slight odor | odorless | very slight odor | slight odor |

TABLE 6

Citric Acid Molar Titrations

| Test Ratio | 0 | 1:1 | 1:1.5 | 1:2 | 1:3 |
|---|---|---|---|---|---|
| pKa | 4.3 | 3.7 | 3.8 | 3.8 | N/A |
| Capacity | 39 | 36 | 38 | 39 | N/A |
| Odor | odorless | odorless | odorless | odorless | odorless |

TABLE 7

Citric Acid Equivalent Titrations

| Test Ratio | 0 | 1:1 | 1:1.5 | 1:2 | 1:3 |
|---|---|---|---|---|---|
| pKa | 4.3 | 3.7 | 3.7 | 3.8 | N/A |
| Capacity | 39 | 36 | 36 | 38 | N/A |
| Odor | odorless | odorless | odorless | odorless | odorless |

EXAMPLES

Example 1. Lactic Acid Complex

Lactic acid and its conjugate base are a commonly used buffer system in feminine hygiene formulations. A preferred lactic acid complex can be prepared on a concentrated basis for formulation and compounding. Buffer formation can be achieved in situ by direct addition of strong base in the formula, alkali contributed by other raw materials or directly by neutralization and isolation of the complex conjugate base post reaction. The complex is prepared by dissolving molar equivalents of α-hydroxy acid in water in the proper proportions with the appropriate molar equivalent of boric acid. Proportions and weights are given in Table 8 for one embodiment of the lactic acid complex.

TABLE 8

Lactic Acid Complex
Complex Ratio 1:1.5

| Ingredient | w/w % |
|---|---|
| Lactic Acid (88%) | 7.794% |
| Boric Acid | 3.138% |
| Water | 89.068% |

The production of the 10% lactic acid complex proved experimentally to be endothermic ($\Delta T=1.7°$ C.). Likewise, the dissolution of boric acid in water was experimentally tested and proved to be endothermic in nature ($\Delta T=1.3°$ C.).

Example 2. In Situ Buffering with Strong Base Detergent

Sodium laureth sulfate, also known as sodium lauryl ether sulfate (SLES), is supplied as the sodium salt at 28-30% active. The pH of commercial SLES is above 10. The monosodium sulfate salt itself is a strong base and there is free sodium hydroxyl, as supplied. Compositions of the preferred complex were prepared in situ by substituting 5% SLES (30%) for water in the dilution table above. Little to no change in buffer characteristics were observed.

TABLE 9

| Test Ratio | 1:1 | 1:1.5 | 1:2 |
|---|---|---|---|
| Lactic Acid Complex | | | |
| pKa | 3.2 | 3.2 | 3.2 |
| Glycolic Acid Complex | | | |
| pKa | 3.2 | 3.2 | 3.3 |
| Citric Acid Complex | | | |
| pKa | 3.6 | 3.7 | 3.7 |

Example 3. In Situ Buffering with Nonionic Emulsifier

Polysorbate 80 is a common nonionic water-soluble emulsifier commonly used in pharmaceutical formulation. Polysorbate 80 is the condensation product of sorbitan monooleate with ethylene oxide, a viscous liquid essentially 100% active. Compositions of an embodiment of a complex were prepared in situ by substituting 0.5% Polysorbate 80 for water in the dilution Table 9 above. Little to no change in buffer characteristics was observed.

TABLE 10

| Test Ratio | 1:1 | 1:1.5 | 1:2 |
|---|---|---|---|
| Lactic Acid Complex | | | |
| pKa | 3.1 | 3.2 | 3.2 |
| Glycolic Acid Complex | | | |
| pKa | 3.2 | 3.3 | 3.3 |
| Citric Acid Complex | | | |
| pKa | 3.7 | 3.7 | 3.7 |

The mono α-hydroxy acid and di α-hydroxy acid complexes of boric acid and its conjugate base provide equivalent buffer capacity to the parent α-hydroxy acid at a lower concentration, surprisingly without changing the buffering range normally associated with the parent α-hydroxy acid. Total concentration of acids, the combined w/w % of boric acid and α-hydroxy acid, does not need to exceed more than about 1.0% w/w % of boric acid and α-hydroxy acid, preferably is below about 0.5 w/w % of boric acid and α-hydroxy acid in a typical skin contact or pharmaceutical formulation and most preferably below about 0.4 w/w % of boric acid and α-hydroxy acid. A preferred composition is any mixture between a range of about 1:1 molar ratio to about 1:2 molar ratio of boric acid to α-hydroxy acid, more preferably between a range of about 1.2 and about 1.8 molar ratio of boric acid to α-hydroxy acid, most preferably between a range of about 1.4 and about 1.6 molar ratio of boric acid to α-hydroxy acid. For ease of identification, the ester as borosesquihydroxycarboxylic acids is identified by their common name (i.e., lactic acid ester is borosesquilactic acid and its conjugate base, borosesquilactate).

The buffers as described herein are useful in many different types of personal care and pharmaceutical formulations intended for human use. The borosesquilactic acid complex was selected for in use formulations due to an observed odor reduction between formulations observed with lactic acid only when compared to wash formulations containing the borosesquilactic acid complex. This odor reducing impact was observed by 5 different trained individuals, each of them noting no lactic acid odor in the wash formulations containing the borosesquilactic acid complex after 0, 1, 2, and 3 months of 40° C./75% RH stability. Furthermore, observations of a lactic acid odor were made on formulations containing only lactic acid on a formulation 2 days after production of the sample. This odor reduction occurs due to the lower volatility of lactic acid when forming the borosesquilactic acid complex with boric acid.

Formulations, as described in Examples 4-9 below, utilizing the borosesquilactic acid complex in various applications were placed on accelerated stability testing at 40° C./75% RH and found stable at 1 month. At 1 month's time there was no detectable sour odor typically associated with lactic acid and the pH was stable with little to no change from the initial time point.

Boric acid has been described by Tepededen, Soya & Korkmaz; *Boric Acid Reduces the Formation of DNA Double Strand Breaks and Accelerates Wound Healing Process* Bioiogical Trace Element Research, 174 (2016), to accelerate and promote wound healing. This process is described through the consumption of boron related compounds in food that are converted in vitro into Boric Acid, allowing for the treatment of inflammation, oxidative stress, and wounds. Although, the borosesquilactic acid and its conjugate base, borosesquilactate complexes, can be utilized in wound healing applications for buffering applications (Example 8), I do not claim unique wound healing properties for the complexes aside from what is found in literature.

Example 4. Cleansing Wash

| Ingredient | w/w % |
| --- | --- |
| Sodium C14-16 Olefin Sulfonate | 20.00% |
| Cocamidopropyl Hydroxy Sultaine | 15.00% |
| Sodium Methyl Cocoyl Taurate | 5.00% |
| Guar Hydroxypropyl Trimonium Chloride | 0.05% |
| Sodium Benzoate | 1.00% |
| Sodium Chloride | 1.00% |
| Lactic Acid Complex (10%) | 10.00% |
| Water | Q.S. |
| | 100.00% |

Processing Instructions: To a clean, dry, glass or stainless-steel vessel add full yield of Purified Water yield. Begin mixing until a vortex is formed using a clean impeller blade. Add sodium benzoate and Edetate Disodium. Mix until incorporated. Premix Guar Hydroxypropyl Trimonium Chloride with Glycereth-26. Add to the center of the vortex. Add Sodium C14-C16 Olefin Sulfonate, Cocamidopropyl Hydroxy Sultaine, and Sodium Methyl Cocoyl Taurate. Mix until fully incorporated. Add Lactic Acid Complex and Sodium Chloride. Mix Well.

TABLE 11

| TIMEPOINT | DESCRIPTION | PH | ODOR |
| --- | --- | --- | --- |
| INITIAL | Slightly Hazy, Slightly Yellow, Viscous, Single Phase Solution | 4.8 | No Lactic Acid Odor |
| 1 MONTH (40° C./75% RH) | Slightly Hazy, Yellow, Viscous, Single Phase Solution | 4.7 | No Lactic Acid Odor |

Example 5. Cleansing Wipe

| Ingredient | w/w % |
| --- | --- |
| Decyl Glucoside | 1.00% |
| Sodium Benzoate | 0.50% |
| Edetate Disodium | 0.50% |
| Lactic Acid Complex (10%) | 1.13% |
| Water | Q.S. |
| | 100.00% |

Processing Instructions: To a clean, dry, glass or stainless-steel vessel add full yield of Purified Water yield. Begin mixing until a vortex is formed using a clean impeller blade. Add Sodium Benzoate and Edetate Disodium. Mix until fully incorporated. Add Decyl Glucoside. Add Lactic Acid Complex. Mix until fully incorporated.

| TIMEPOINT | DESCRIPTION | PH | ODOR |
| --- | --- | --- | --- |
| INITIAL | Clear, Colorless, Single Phase Solution | 4.8 | No Lactic Acid Odor |
| 1 MONTH (40° C./75% RH) | Clear, Colorless, Single Phase Solution | 4.8 | No Lactic Acid Odor |

Example 6. Moisturizing Lotion

| Ingredient | w/w % |
| --- | --- |
| Acrylates/C10-C30 Alkyl Acrylate Crosspolymer | 0.55% |
| Sunflower Seed Oil | 1.00% |
| PEG-40 HCO | 0.50% |
| Aminomethyl propanol 2000 | 0.90% |

| Ingredient | w/w % |
|---|---|
| Sorbitol Monolaurate | 1.00% |
| Hemisqualane | 2.50% |
| Phenoxyethanol | 0.75% |
| Lactic Acid Complex (10%) | 4.00% |
| Water | Q.S. |
| | 100.00% |

Processing Instructions: Phase 1—To a clean, dry, glass or stainless-steel vessel add full yield of Purified Water yield. Begin mixing until a vortex is formed using a clean paddle blade. Add Lactic Acid Complex, Acrylates/C10-C30 Alkyl Acrylate Cross polymer, and Phenoxyethanol. Mix until fully incorporated. Add Prewarmed PEG-40 Hydrogenated Castor Oil.
Phase 2—In a separate clean dry glass or stainless-steel vessel, add Sorbitan Monolaurate, hemisqualene, and sunflower seed oil. Mix until homogenous. Slowly add Phase 2 to Phase 1 with constant mixing. Add aminomethyl propanol 2000. Mix until homogenous.

| TIMEPOINT | DESCRIPTION | PH | ODOR |
|---|---|---|---|
| INITIAL | White Opaque Cream | 4.5 | No Lactic Acid Odor |
| 1 MONTH (40° C./75% RH) | White Opaque Cream | 4.5 | No Lactic Acid Odor |

Example 7. Feminine Cleansing Douche

| Ingredient | w/w % |
|---|---|
| Sodium Benzoate | 1.00% |
| Edetate Disodium | 0.50% |
| Vinegar, 10% | 0.50% |
| Lactic Acid Complex (10%) | 5.00% |
| Water | Q.S. |
| | 100.00% |

Processing Instructions: To a clean, dry, glass or stainless-steel vessel add full yield of Purified Water yield. Begin mixing until a vortex is formed using a clean impeller blade. Add Sodium Benzoate and Edetate Disodium. Mix until fully incorporated. Add Vinegar, 10% and Lactic Acid Complex. Mix Well.

| TIMEPOINT | DESCRIPTION | PH | ODOR |
|---|---|---|---|
| INITIAL | Clear, Colorless, Single Phase Solution | 3.8 | No Lactic Acid Odor |
| 1 MONTH (40° C./75% RH) | Clear, Colorless, Single Phase Solution | 3.8 | No Lactic Acid Odor |

Example 8. Wound Cream

| Ingredient | w/w % |
|---|---|
| Glycerin | 5.00% |
| Dipalmitoylethyl Hydroxyethylmonium Methosulfate | 3.00% |
| Emulsifying Wax, NF | 3.50% |
| Isopropyl Myristate | 3.00% |
| Dimethicone | 1.25% |
| Cetyl Alcohol | 2.00% |
| Lanolin | 2.00% |
| Potassium Chloride | 0.35% |
| Lactic Acid Complex (10%) | 1.00% |
| Water | Q.S. |
| | 100.00% |

Processing Instructions: Phase 1—To a clean, dry, glass or stainless-steel vessel add full yield of Purified Water yield. Begin mixing until a vortex is formed using a clean paddle blade. Add Glycerin and Dipalmitoylethyl Hydroxyethylmonium Methosulfate. Begin to Mix and Heat to 70-75° C.
Phase 2—In a separate vessel, prepare the oil phase by adding Emulsifying Wax, NF, Isopropyl Myristate Dimethicone, Lanolin, and Cetyl Alcohol. Heat to 70-75° C. with continuous mixing. Add Phase 2 to Phase 1. Allow to cool slowly under constant mixing to 40-45° C. Add Potassium Chloride and Lactic Acid Complex. Continue to mix until the batch reaches 30° C. and stop mixing.

| TIMEPOINT | DESCRIPTION | PH | ODOR |
|---|---|---|---|
| INITIAL | Thick, Opaque White Cream | 4.5 | No Lactic Acid Odor |
| 1 MONTH (40° C./75% RH) | Thick, Opaque White Cream | 4.4 | No Lactic Acid Odor |

Example 9. Personal Lubricant

| Ingredient | w/w % |
|---|---|
| Sodium Benzoate | 0.50% |
| Xanthan Gum | 1.00% |
| Hyaluronic Acid | 0.50% |
| Aloe Vera Gel | 0.50% |
| Lactic Acid Complex | 1.00% |
| Water | Q.S. |
| | 100.00% |

| TIMEPOINT | DESCRIPTION | PH | ODOR |
|---|---|---|---|
| INITIAL | Slightly Hazy Gel | 4.8 | No Lactic Acid Odor |
| 1 MONTH (40° C./75% RH) | Slightly Hazy Gel | 4.8 | No Lactic Acid Odor |

Processing Instructions: To a clean, dry, glass or stainless-steel vessel add full yield of Purified Water yield, Aloe Vera Gel, and Lactic Acid Complex. Begin mixing until a vortex is formed using a clean paddle blade. Add Sodium Benzoate. Mix until fully incorporated. Begin heating to 40-40° C., add hyaluronic acid. Mix until homogenous. Slowly add Xanthan Gum. Mix until fully incorporated.

I claim:

1. A composition for use as a buffer in personal care and pharmaceutical formulations, the composition comprising:
   esters of boric acid and α-hydroxy monocarboxylic acids having 2 to 12 carbon atoms; and
   corresponding basic conjugate salts of esters of boric acid and α-hydroxy monocarboxylic acids having 2 to 12 carbon atoms, wherein the molar ratio of boric acid to α-hydroxy acid is between about 1:1 and about 1:2, and wherein the weight of boric acid and α-hydroxy acid is up to about 1.0% by weight (w/w %) of the composition.

2. A composition for use as a buffer in personal care and pharmaceutical formulations, the composition comprising:
   esters of boric acid and α-hydroxy monocarboxylic acids having 2 to 12 carbon atoms; and
   corresponding basic conjugate salts of esters of boric acid and α-hydroxy monocarboxylic acids having 2 to 12 carbon atoms, wherein the molar ratio of boric acid to α-hydroxy acid is between about 1:1 and about 1:2, and wherein the weight of boric acid and α-hydroxy acid is up to about 0.5% by weight (w/w %) of the composition.

3. A composition for use as a buffer in personal care and pharmaceutical formulations, the composition comprising:
   esters of boric acid and α-hydroxy monocarboxylic acids having 2 to 12 carbon atoms; and
   corresponding basic conjugate salts of esters of boric acid and α-hydroxy monocarboxylic acids having 2 to 12 carbon atoms, wherein the molar ratio of boric acid to α-hydroxy acid is between about 1:1 and about 1:2, and wherein the weight of boric acid and α-hydroxy acid is up to about 0.4% by weight (w/w %) of the composition.

4. A composition for use as a buffer in personal care and pharmaceutical formulations, the composition comprising:
   esters of boric acid and α-hydroxy monocarboxylic acids having 2 to 12 carbon atoms; and
   corresponding basic conjugate salts of esters of boric acid and α-hydroxy monocarboxylic acids having 2 to 12 carbon atoms,
   wherein the molar ratio of boric acid to α-hydroxy acid is between about 1:1.2 and about 1:1.8.

5. A composition for use as a buffer in personal care and pharmaceutical formulations, the composition comprising:
   esters of boric acid and α-hydroxy monocarboxylic acids having 2 to 12 carbon atoms; and
   corresponding basic conjugate salts of esters of boric acid and α-hydroxy monocarboxylic acids having 2 to 12 carbon atoms,
   wherein the molar ratio of boric acid to α-hydroxy acid is between about 1:1.4 and about 1:1.6.

6. A formulation for topical application for use as a personal lubricant, the formulation comprising the composition as recited in claim 1 up to about 1% by weight of the formulation, and further comprising
   sodium benzoate up to about 0.50% by weight of the formulation,
   xanthan gum up to about 1.0% by weight of the formulation,
   hyaluronic acid up to about 0.5% by weight of the formulation, and
   aloe vera gel up to about 0.5% by weight of the formulation.

7. The personal lubricant formulation as recited in claim 6, wherein the composition comprises a boric acid lactic acid ester buffer.

8. A formulation for use as a wound cream, the formulation comprising the composition as recited in claim 1 up to about 1% by weight of the formulation, and further comprising
   glycerin up to about 5% by weight of the formulation,
   dipalmitoylethyl hydroxyethylmonium methosulfate up to about 3% by weight of the formulation,
   emulsifying wax up to about 3.5% by weight of the formulation,
   isopropyl myristate up to about 3% by weight of the formulation,
   dimethicone up to about 1.25% by weight of the formulation,
   cetyl alcohol up to about 2% by weight of the formulation,
   lanolin up to about 2% by weight of the formulation, and
   potassium chloride up to about 0.35% by weight of the formulation.

9. The wound cream formulation as recited in claim 8, wherein the composition comprise a boric acid lactic acid ester buffer.

10. A formulation for use as a feminine cleansing douche, the formulation comprising the composition as recited in claim 1 up to about 5% by weight of the formulation, and further comprising
    sodium benzoate up to about 1% by weight of the formulation,
    edetate disodium up to about 0.5% by weight of the formulation, and
    vinegar up to about 0.5% by weight of the formulation.

11. The feminine cleansing douche formulation as recited in claim 10, wherein the composition comprises a boric acid lactic acid ester buffer.

12. A formulation for use as a moisturizing lotion, the formulation comprising the composition as recited in claim 1 up to about 4% by weight of the formulation, and further comprising
    acrylates up to about 0.55% by weight of the formulation,
    sunflower seed oil up to about 1% by weight of the formulation,
    PEG 40 HCO up to about 0.5% by weight of the formulation,
    aminomethyl propanol 2000 up to about 0.9% by weight of the formulation,
    sorbitol monolaurate up to about 1% by weight of the formulation,
    hemisqualane up to about 2.5% by weight of the formulation, and
    phenoxyethanol up to about 0.75% by weight of the formulation.

13. The moisturizing lotion formulation as recited in claim 12, wherein the acrylates comprise C10-C30 alkyl acrylate crosspolymer.

14. The moisturizing lotion formulation as recited in claim 12, wherein the composition comprises a boric acid lactic acid ester buffer.

15. A formulation for use as a wipe, the formulation comprising the composition as recited in claim 1 up to about 1.13% by weight of the formulation, and further comprising
    decyl glucoside up to about 1% by weight of the formulation,
    sodium benzoate up to about 0.5% by weight of the formulation, and
    edetate disodium up to about 0.5% by weight of the formulation.

16. The wipe formulation as recited in claim 15, wherein the composition comprises a boric acid lactic acid ester buffer.

17. A formulation for use as a cleansing wash, the formulation comprising the composition as recited in claim 1 up to about 10% by weight of the formulation, and further comprising sodium c14-c16 olefin sulfonate up to about 20% by weight of the formulation, cocamidopropyl hydroxy sultaine up to about 15% by weight of the formulation, sodium methyl cocoyl taurate up to about 5% by weight of the formulation, Guar Hydroxypropyl Trimonium Chloride up to about 0.05% by weight of the formulation, sodium benzoate up to about 1% by weight of the formulation, and sodium chloride up to about 1% by weight of the formulation.

18. The cleansing wash formulation as recited in claim 17, wherein the composition comprises a boric acid lactic acid ester buffer.

19. A method of treating the skin comprising the step of topically applying onto the skin an effective amount of the composition as recited in claim 1.

20. The composition as recited in claim 1, wherein the composition is in the acidic range of about 3.8-5.8 and the corresponding salts are in the basic range of about 8.2-10.2.

21. The composition as recited in claim 1, wherein the composition is in the acidic range of about 4.0-5.5 and the corresponding salts are in the basic range of about 8.4-9.9.

\* \* \* \* \*